United States Patent
Graham et al.

(10) Patent No.: US 11,479,788 B2
(45) Date of Patent: Oct. 25, 2022

(54) TOMATO PLANTS WITH IMPROVED DISEASE RESISTANCE

(71) Applicant: Seminis Vegetable Seeds, inc., St. Louis, MO (US)

(72) Inventors: Elaine Graham, Davis, CA (US); Albert Grit, Ermelo (NL); Gregory Pape, St. Louis, MO (US); Stephanie J. Pedroni, St. Louis, MO (US); Marilyn West, St. Louis, MO (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 16/218,261

(22) Filed: Dec. 12, 2018

(65) Prior Publication Data

US 2019/0211351 A1    Jul. 11, 2019

Related U.S. Application Data

(60) Provisional application No. 62/598,183, filed on Dec. 13, 2017.

(51) Int. Cl.
| | |
|---|---|
| *A01H 5/08* | (2018.01) |
| *A01H 6/82* | (2018.01) |
| *C12N 15/82* | (2006.01) |
| *C12Q 1/686* | (2018.01) |
| *C12Q 1/6895* | (2018.01) |

(52) U.S. Cl.
CPC .......... *C12N 15/8282* (2013.01); *A01H 5/08* (2013.01); *A01H 6/825* (2018.05); *C12Q 1/686* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,100,449 A | 8/2000 | Fluhr et al. | |
| 7,205,451 B2 | 4/2007 | Haring et al. | |
| 8,097,789 B2* | 1/2012 | Heath | A01H 5/08 435/411 |
| 8,097,791 B2* | 1/2012 | Heath | A01H 1/02 800/317.4 |
| 10,813,339 B2 | 10/2020 | Kramer | |
| 2011/0094194 A1 | 4/2011 | Cook | |
| 2015/0121559 A1 | 4/2015 | Frantz | |

FOREIGN PATENT DOCUMENTS

WO    WO 1997/006259    2/1997

OTHER PUBLICATIONS

Lim et al. High resolution genetic and physical mapping of the I-3 region of tomato chromosome 7 reveals almost continuous microsynteny with grape chromosome 12 but interspersed microsynteny with duplications on *Arabidopsis* chromosomes 1, 2 and 3. Theor. Appl. Genet. 2008. 118:57-75.*
Li et al. Linkage between the I-3 gene for resistance to Fusarium wilt race 3 and increased sensitivity to bacterial spot in tomato. Theor. Appl. Genet. 2018. 131:145-155.*
Cantanzariti et al. The tomato I-3 gene: a novel gene for resistance to Fusarium wilt disease. New Phytologist. 2015. 207:106-118.*
Gen Bank Accession No. CP023763. Solanum lycopersicum cultivar I-3 chromosome 7. Published Nov. 3, 2017. pp. 1.*
Bortesi et al. The CRISPR/Cas9 system for plant genome editing and beyond. Biotechnology Advances. 2015. 41-52.*
Aoki, et al., "Large-Scale Analysis of Full-Length CDNAs from Tomato (*Solanum lycopersicum*) Cultivar Micro-Tom, a Reference System for the Solanaceae Genomics," BMC Genomics 11:210 (2010).
Bournival, et al., "An Isozyme Marker for Resistance to Race 3 of *Fusarium oxysporum* f. sp. *lycopersici* in Tomato," Theor Appl Genet 78(4):489-494 (1989).
Hemming, et al., "Fine Mapping of the Tomato I-3 Gene for Fusarium wilt Resistance and Elimination of Co-Segregating Resistance Gene Analogue as a Candidate for I-3," Theor Appl Genet 109:409-418 (2004).
International Search Report and Written Opinion regarding International Application No. PCT/2018/06511, dated Mar. 11, 2019.
Lim, et al., "High Resolution Genetic and Physical Mapping of the I-3 Region of Tomato Chromosome 7 Reveals Almost Continuous Microsynteny with Grape Chromosome 12 but Interspersed Microsynteny with Duplications on *Arabidopsis* chromosomes 1, 2 and 3," Theor Appl Genet 118(1):57-75 (2008).
Tanksley, et al., "High Density Molecular Linkage Maps of the Tomato and Potato Genomes," Genetics 132(4):1141-1160 (1992).
GenBank Accession No. AK327925, dated May 1, 2010.
U.S. Appl. No. 16/513,138, filed Jul. 16, 2019, Kramer.
U.S. Appl. No. 16/513,109, filed Jul. 16, 2019, Kramer.
U.S. Appl. No. 16/721,487, filed Dec. 19, 2019, Krivanek.
U.S. Appl. No. 16/783,770, filed Feb. 6, 2020, Krivanek.
U.S. Appl. No. 16/936,129, filed Jul. 22, 2020, Kramer.
U.S. Appl. No. 16/936,201, filed Jul. 22, 2020, Kramer.
U.S. Appl. No. 17/024,130, filed Sep. 17, 2020, Krivanek.

* cited by examiner

*Primary Examiner* — Jason Deveau Rosen
(74) *Attorney, Agent, or Firm* — Dentons US LLP; Matthew Madsen

(57) ABSTRACT

Tomato plants exhibiting resistance to *Fusarium oxysporum* f. sp. *lycopersici* (Fol) are provided, together with methods of producing, identifying, or selecting plants or germplasm with a Fol resistance phenotype and lacking undesirable soft fruit traits. Such plants include tomato plants comprising introgressed genomic regions conferring disease resistance. Compositions, including novel polymorphic markers for detecting plants comprising introgressed disease resistance alleles, are further provided.

10 Claims, 1 Drawing Sheet
Specification includes a Sequence Listing.

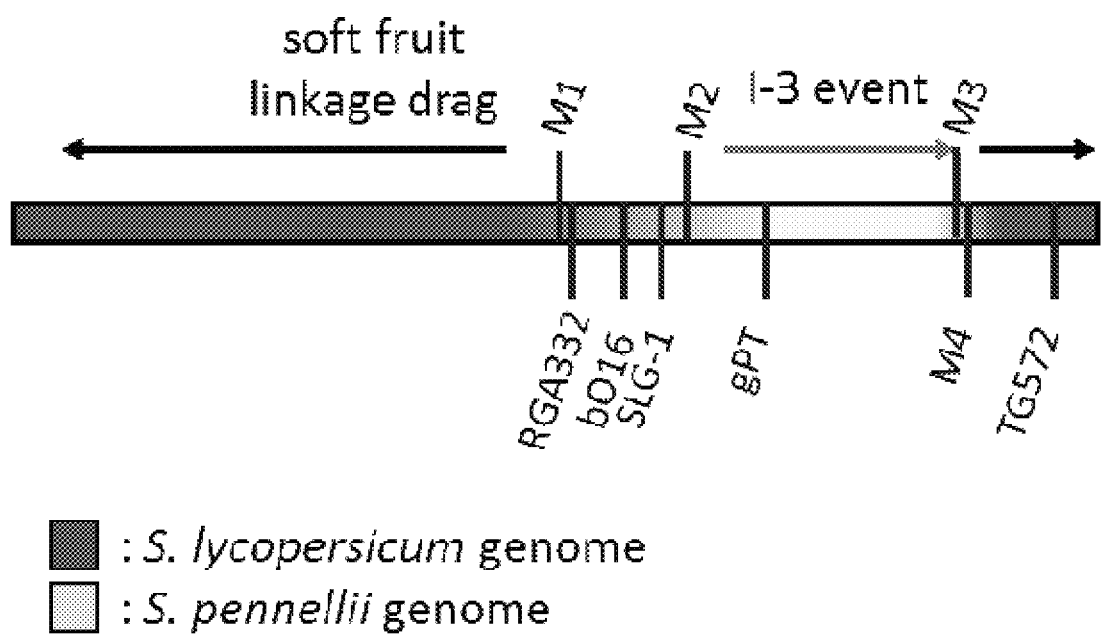

SEQUENCE LISTING

```
<160> NUMBER OF SEQ ID NOS: 12

<210> SEQ ID NO 1
<211> LENGTH: 643
<212> TYPE: DNA
<213> ORGANISM: Solanum pennellii
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(197)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (265)..(265)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
```

```
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t

<400> SEQUENCE: 1
ttcatgggaa atantctgtc agggctcatg ttatttctgc gatgaactac tattccaaat      60
ctatgttatg acagttctcc ctatcaatac aattcccctt cattcatttt aagctctcaa     120
aatragtaaa gatgaaaaaa ggagtatacc aactgatgta ctcngtagtt gtttatattc     180
taaatcagcc tntannnttc tttttcngtc tttgtttgtt aacttgtaga tctaaagttg     240
gttaatgcat cntccacaaa atttngcttc tctataacna tgtctcactt cnccttgcta     300
aattctcttt acccatactt gcaagntcca tgatcatatc tgcaactaac ttgcagtccg     360
aaagctgcag cttcagcctc agctacattg ttactacaaa gcattgcaaa angccaaata     420
ctcattgatc cctnatatct ttctgtatgc ctcattatat tccaaaataa attcagtgtc     480
tcaacagctt gtgggaattc agaaattcnt ggaaaagacg ggcttcaggg aacttgtttt     540
aaaccatctc tgctgtacat ttngtttgnc atggttataa ttacaaatca tttagatcta     600
atcgagaaag aggaaactcc tgctttattg aaatttaggc aaa                      643

<210> SEQ ID NO 2
<211> LENGTH: 29
<212> TYPE: DNA
<213> ORGANISM: Artificial sequence
<220> FEATURE:
<223> OTHER INFORMATION: Primer

<400> SEQUENCE: 2
acaattcccc ttcattacat ttaagctct                                        29

<210> SEQ ID NO 3
<211> LENGTH: 30
<212> TYPE: DNA
<213> ORGANISM: Artificial sequence
<220> FEATURE:
<223> OTHER INFORMATION: Primer

<400> SEQUENCE: 3
gatgcattaa ccaactttag atctacaagt                                       30

<210> SEQ ID NO 4
<211> LENGTH: 24
```

<212> TYPE: DNA
<213> ORGANISM: Artificial sequence
<220> FEATURE:
<223> OTHER INFORMATION: Probe

<400> SEQUENCE: 4
cttttttcat ctttacttat tttg                                     24

<210> SEQ ID NO 5
<211> LENGTH: 21
<212> TYPE: DNA
<213> ORGANISM: Artificial sequence
<220> FEATURE:
<223> OTHER INFORMATION: Probe

<400> SEQUENCE: 5
ttttcatctt tactcatttt g                                        21

<210> SEQ ID NO 6
<211> LENGTH: 547
<212> TYPE: DNA
<213> ORGANISM: Solanum pennellii
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t

<400> SEQUENCE: 6
atttntgtac ataaaacgcg attttttttnc cctttagcaa cagctggttt agcttaaacc    60 tgtacttta taaacgcgac agagtcatac cttgtcttgt ccttctcatt attcattagt    120
garaagatct cagttggtaa gtagcactcc cctatggccc tggaagaatt taaaccacta    180
cgaaagaacg cagctttaca ggaacattta tccaaacatg cgcgtttaca agtantcaca    240
tctgtgttgc tgtatatctgc agtaaacgcg aaatagtcca catcttcaac ttccaaaagt    300
ctgtgtttct ttaagttgtt gcaactcagc ttttttggcct cagagcaacc nagattaggc    360
agcctaacnt ttatcggtct gaaataggta gttgaattag agcttatggg acaactacat    420
tgtcccattg tgcaaatgcc atatcttcca cagactgtag ggtaattgca ctcgccacga    480
aagcctgtta agagntcatc cacctctctc catcgacttn tccactcgta cactttcaag    540
tgtccgt                                                              547

<210> SEQ ID NO 7

<210> SEQ ID NO 8
<211> LENGTH: 22
<212> TYPE: DNA
<213> ORGANISM: Artificial sequence
<220> FEATURE:
<223> OTHER INFORMATION: Primer

<400> SEQUENCE: 8
gggagtgcta cttaccaact ga                                    22

<210> SEQ ID NO 9
<211> LENGTH: 19
<212> TYPE: DNA
<213> ORGANISM: Artificial sequence
<220> FEATURE:
<223> OTHER INFORMATION: Probe

<400> SEQUENCE: 9
attcattagt gaaaagatc                                         19

<210> SEQ ID NO 10
<211> LENGTH: 17
<212> TYPE: DNA
<213> ORGANISM: Artificial sequence
<220> FEATURE:
<223> OTHER INFORMATION: Probe

<400> SEQUENCE: 10
tcattagtga gaagatc                                           17

<210> SEQ ID NO 11
<211> LENGTH: 201
<212> TYPE: DNA
<213> ORGANISM: Solanum pennellii
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (169)..(170)
<223> OTHER INFORMATION: n is a, c, g, or t

<400> SEQUENCE: 11
cncacaattg aattcagtat atnaaagtgg aaagcaaat caaatgaaaa agattcaaaa    60
ttgcanttcc aaaactcccc ctcagtcatt atttatggga yattttcct tacagagtta   120 atatgactaa tttcaaagct aaattggaaa tatnttaaa atttaaaann tttagacatt   180

```
caaaaattat actagttcat c                                                   201

<210> SEQ ID NO 12
<211> LENGTH: 201
<212> TYPE: DNA
<213> ORGANISM: Solanum pennellii

<400> SEQUENCE: 12
aattctttca caattcaaat acttacctttt gaatatctag ggtcaatttc aatagctcta        60
gttccatcct gtattgcgct tccatattcc tccaatttgg wgtgagcaaa cgcacggtta        120
gcatagtaca ccgcattctc accgttcaac tcaatcgctt gtgtgtacag atcaatagct        180
tgcgaatact tatgccctga a                                                   201
```

TOMATO PLANTS WITH IMPROVED DISEASE RESISTANCE

CROSS-REFERENCE TO RELATED APPLICATIONS

This application claims the priority of U.S. Provisional Appl. Ser. No. 62/598,183, filed Dec. 13, 2017, which is incorporated herein by reference in its entirety.

INCORPORATION OF SEQUENCE LISTING

A sequence listing containing the file named "SEMB032US_ST25.txt" which is 7 kilobytes (measured in MS-Windows®) and created on Dec. 10, 2018.

FIELD OF THE INVENTION

The present invention relates to the field of plant breeding and more specifically to methods and compositions for producing tomato plants exhibiting improved disease resistance.

BACKGROUND

Disease resistance is an important trait in agriculture, particularly for the production of food crops. Although disease resistance alleles have been identified in tomato, efforts to introduce these alleles into cultivated lines have been hindered by a lack of specific markers linked to the alleles, as well as the presence of deleterious alleles genetically linked to disease resistance alleles that lead to unacceptable fruit quality. The use of marker-assisted selection (MAS) in plant breeding has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis, and an often incomplete understanding of the genetic background underlying expression of a desired phenotype. In the absence of accurate and validated markers for use in MAS, it may not be feasible to produce new plant lines exhibiting certain disease resistance phenotypes and acceptable fruit quality.

SUMMARY

In one aspect, tomato plants of a cultivated variety are provided comprising a recombinant chromosomal segment on chromosome 7, wherein said chromosomal segment comprises a *Fusarium oxysporum* f. sp. *lycopersici* (Fol) resistance allele conferring to said plant increased resistance to Fol compared to a plant not comprising said allele, and wherein said chromosomal segment lacks a deleterious allele genetically linked to said Fol resistance allele that confers a soft fruit trait to said plant when present. In some embodiments, said recombinant chromosomal segment is flanked in the genome of said plant by marker locus M1 (SEQ ID NO:1) and marker locus M3 (SEQ ID NO:11) on chromosome 7. In further embodiments, said introgressed Fol resistance allele is within a recombinant chromosomal segment on chromosome 7 comprising marker locus M2 (SEQ ID NO:6). Tomato plants provided herein may comprise: a) a non-introgressed allele at marker locus M1 (SEQ ID NO:1); and b) an introgressed allele at marker locus M2 (SEQ ID NO:6). In some embodiments tomato plants provided further comprise a non-introgressed allele at marker locus M4 (SEQ ID NO:12). Plant parts of tomato plants provided herein are further provided.

In another aspect, tomato plants are provided wherein a representative sample of seed comprising said chromosomal segment has been deposited under Accession No. PTA-124465. In some embodiments, said chromosomal segment is derived from a plant of line FDS-ZJ11002. Tomato plants, cells, or seeds of tomato line FDS-ZJ11002 are provided, wherein a sample of seed of said line has been deposited under ATCC Accession No. PTA-124465.

In a further aspect, a recombinant DNA segment is provided comprising a Fol resistance allele that confers to a plant increased resistance to Fol, and lacking a deleterious allele genetically linked to said Fol resistance allele that confers to a plant a soft fruit trait. In some embodiments, said recombinant DNA segment comprises marker M2 (SEQ ID NO:6). In further embodiments, said recombinant DNA segment is further defined as comprised within a plant, plant part, plant cell, or seed. In yet further embodiments, said DNA segment confers increased resistance to Fol to said plant.

In another aspect, methods are provided for producing a tomato plant exhibiting resistance to Fol, comprising: a) crossing a tomato plant provided herein with itself or with a second tomato plant of a different genotype to produce one or more progeny plants; and b) selecting a progeny plant comprising said Fol resistance allele. In some embodiments, selecting said progeny plant comprises detecting a marker locus genetically linked to said Fol resistance allele. In other embodiments, selecting said progeny plant comprises detecting a marker locus within or genetically linked to a chromosomal segment flanked in the genome of said plant by marker locus M2 (SEQ ID NO:6) and marker locus M3 (SEQ ID NO:11) on chromosome 7. In further embodiments, selecting a progeny plant comprises detecting at least one polymorphism at a locus selected from the group consisting of marker locus M1 (SEQ ID NO:1), marker locus M2 (SEQ ID NO:6), marker locus M3 (SEQ ID NO:11), and marker locus M4 (SEQ ID NO:12). In yet further embodiments, selecting a progeny plant comprises detecting: a) a polymorphism at marker locus M1 (SEQ ID NO:1) and marker locus M2 (SEQ ID NO:6); orb) a polymorphism at marker locus M3 (SEQ ID NO:11) and marker locus M4 (SEQ ID NO:12). In certain embodiments, selecting a progeny plant comprises detecting: a) a recurrent parent allele at marker locus M1 (SEQ ID NO:1); and b) a donor allele at marker M2 (SEQ ID NO:6). In further embodiments, selecting a progeny plant further comprises detecting: a) a donor allele at marker locus M3 (SEQ ID NO:11); and b) a recurrent parent allele at marker M4 (SEQ ID NO:12). In some embodiments, said progeny plant is an $F_2$-$F_6$ progeny plant or producing said progeny plant comprises backcrossing.

In a further aspect, methods are provided of producing a tomato plant exhibiting resistance to Fol, comprising introgressing into a plant a Fol resistance allele within a recombinant chromosomal segment flanked in the genome of said plant by: marker locus M1 (SEQ ID NO:1) and marker locus M3 (SEQ ID NO:11) on chromosome 7; wherein said introgressed Fol resistance allele confers to said plant increased resistance to Fol compared to a plant not comprising said allele, and wherein said recombinant chromosomal segment lacks a deleterious allele genetically linked to said Fol resistance allele that confers a soft fruit trait to said plant when present. In certain embodiments, said introgressed Fol resistance allele is within a recombinant chromosomal segment on chromosome 7 comprising marker locus M2 (SEQ ID NO:6). In some embodiments, said recombinant chromosomal segment is defined by: a) a non-introgressed allele at marker locus M1 (SEQ ID NO:1); and b) an introgressed allele at marker locus M2 (SEQ ID NO:6). Said introgressing may comprise backcrossing, marker-assisted selection, or assaying for said Fol resistance. Tomato plants obtainable by the methods disclosed herein are further provided.

In yet a further aspect, methods are provided of producing a tomato plant exhibiting resistance to Fol, comprising: a) crossing a tomato plant provided herein with itself or with a second tomato plant of a different genotype to produce one or more progeny plants; and b) selecting a progeny plant comprising said Fol resistance allele. In certain embodiments, selecting said progeny plant comprises detecting a marker locus genetically linked to said Fol resistance allele. In some embodiments, selecting said progeny plant comprises detecting a marker locus within or genetically linked to a chromosomal segment flanked in the genome of said plant marker locus M1 (SEQ ID NO:1) and marker locus M3 (SEQ ID NO:11) on chromosome 7. In further embodiments, selecting a progeny plant comprises detecting at least one polymorphism at a locus selected from the group consisting of marker locus marker locus M1 (SEQ ID NO:1), marker locus M2 (SEQ ID NO:6), marker locus M3 (SEQ ID NO:11), and marker locus M4 (SEQ ID NO:12). In yet further embodiments, said progeny plant is an $F_2$-$F_6$ progeny plant, or producing said progeny plant comprises backcrossing.

BRIEF DESCRIPTION OF THE DRAWINGS

FIG. 1 shows the relative positioning of markers developed by the inventors related to publicly available markers used in the fine-mapping of the I-3 locus.

DETAILED DESCRIPTION

*Fusarium oxysporum* f sp. *lycopersici* (Fol) is a fungal pathogen that causes *Fusarium* wilt in tomato plants (*Solanum lycopersicum*), and this damaging pathogen has spread throughout all major tomato production regions of the world. Three races for Fol have been identified, known in the United States as Fol:1, Fol:2, and Fol:3 (referred to in Europe as Fol:0, Fol:1, and Fol:2, respectively). Single dominant genetic loci designated I, 1-2, and most recently I-3, have been identified that confer resistance against Fol:1, Fol:2, and Fol:3, respectively.

The I-3 gene was originally identified in the wild tomato accession *Solanum pennellii* LA0716 (Available from the Tomato Genetic Resource Center in Davis, Ca, USA). Subsequent mapping efforts have determined that the I-3 locus is located within a 0.3 cM region on chromosome 7 of the *S. lycopersicum* genome. However, the mapping populations used in previous studies involved at most one backcross and therefore contained a large amount of wild *S. pennellii* DNA. Therefore, previous studies failed to identify, map, and provide a method to remove the deleterious soft fruit trait tightly associated with the I-3 gene, which is most apparent in elite lines with commercial quality fruit.

Efforts have been made to introgress the Fol:3 resistance gene I-3 from resistant tomato lines into other cultivated tomato lines. However, this has always been with a larger sized introgression and at the cost of product quality due to the association of introgressed disease resistance alleles with undesirable agronomic traits such as soft fruit. Tomato growers with Fol:3 in their fields so far have had to compromise between lower fruit quality and yield loss due to Fol, making them less competitive in the marketplace. It is important that tomato growers can determine a good moment for harvest, for example when the processing plant requests the fruit, or when the market prices are highest, and to be able to deliver a tomato product of acceptable quality that meets market specifications. In certain markets, soft fruit is not acceptable due to consumer desires or firmness specifications for shipping/transportation needs. In other cases, the soft fruit characteristics associated with the I-3 gene can lead to quickened fruit quality deterioration and increased likelihood of subsequent fruit rot and/or mold, ultimately leading to reduced field holding and storage ability. In either case, this often leads to lower prices for their crop or even rejected harvests because of an unacceptably high percentage of moldy fruit or poorer quality fruit for the consumer. A FOL:3 resistant tomato plant without this limiting soft fruit linkage drag is therefore in high demand among growers.

The introgression of the I-3 locus into elite germplasm was shown by the present inventors to be associated with a commercially unacceptable soft fruit trait that results in several issues that reduce marketability of the fruit, such as fruit damage during transport, and quickened deterioration of fruit when ripe. Efforts to reduce the incidence or severity of the undesirable soft fruit trait in tomato plants comprising Fol resistance introgressions have been hindered by an incomplete understanding of the genetic factors controlling Fol resistance. In particular, markers and assays that accurately correlate genotype with disease resistance and fruit yield phenotypes over a variety of tomato types have previously been unavailable.

The present inventors have for the first time mapped the deleterious soft fruit alleles associated with the I-3 disease resistance locus, and identified novel genetic markers for identifying and tracking the I-3 and soft fruit loci during plant breeding. Having discovered the I-3 disease resistance alleles and the soft fruit alleles can be unlinked using the novel markers provided herein, the inventors created for the first time a breeding event that can be used by breeders to easily transfer the I-3 resistance alleles without the soft fruit trait to other tomato plants.

The present inventors have discovered for the first time that M1, a SNP marker with a [A/G] change at 60,912,462 bp on chromosome 7 of version SL2.40 of the public genome, is linked to deleterious soft fruit alleles, while Marker M2, a SNP marker with a [A/G] change at 60,956,224 bp on chromosome 7 of version SL2.40 of the public genome, is linked to the I-3 resistance gene. The public genome of tomato is available at for example www.solgenomics.net, and one skilled in the art would understand that the marker sequences provided for the first time in the instant application could be located on any version (or later version) of the public genome. The invention therefore provides plants comprising recurrent parent DNA at marker locus M1 (SEQ ID NO:1), and introgressed donor DNA at marker locus M2 (SEQ ID NO:6). In further embodiments, the invention provides plants comprising introgressed donor DNA at marker locus M3, a SNP marker with a [C/T] change at 61,095,125 bp on chromosome 7, and recurrent parent DNA at marker locus M4, a SNP marker with a [A/T] change at 61,106,828 bp on chromosome 7.

In certain embodiments, tomato plants are provided comprising an introgressed allele on chromosome 7, wherein said introgressed allele confers to said plant increased resistance to Fol compared to a plant not comprising said allele. In further embodiments, said plant lacks a further allele, genetically linked to said introgressed allele, that confers decreased fruit quality when present. In some embodiments said further allele confers a soft fruit trait when present.

The invention further provides reduced recombinant introgressions comprising a genomic interval between marker locus M2 (SEQ ID NO:6) and marker locus M3 (SEQ ID NO:11) on chromosome 7, wherein said reduced genomic interval lacks deleterious soft fruit alleles associated with larger Fol resistance introgressions.

In other embodiments, the invention provides plants comprising one or more of the novel recombinant introgressions provided herein. These novel introgressions provide robust resistance to Fol, while avoiding the reduction in performance characteristics associated with conventional introgressions of the I-3 gene. Methods of producing the plants described herein are further provided. In certain embodiments, the invention provides tomato line FDS-ZJ11002 comprising an exemplary reduced introgression described herein, a sample of the seed of which has been deposited under ATCC Accession No. PTA-124465.

The invention further provides novel trait-linked markers which can be used to produce plants comprising novel recombinant introgressions on chromosome 7 conferring Fol resistance as described herein. In particular embodiments, the invention provides the markers shown in Table 1

Methods of producing plants comprising the reduced recombinant introgressions described herein are further provided. In some examples, donor DNA from a resistant donor parent is introgressed into a cultivated plant line (the recurrent parent line). M1 (SEQ ID NO:1) is used to select the allele of the recurrent parent and M2 (SEQ ID NO:6), is used to select the allele of the resistance donor parent resulting in a reduced genomic interval lacking deleterious traits associated with larger Fol resistance introgressions. In further embodiments, M3 (SEQ ID NO:11) is further used to select the allele of the resistance donor parent, and M4 (SEQ ID NO:12) is further used to select the allele of the recurrent parent resulting in a reduced genomic interval conferring Fol resistance.

In certain embodiments, the invention provides methods of producing or selecting a tomato plant exhibiting resistance to Fol comprising: a) crossing a tomato plant provided herein with itself or with a second tomato plant of a different genotype to produce one or more progeny plants; and b) selecting a progeny plant comprising said first introgressed allele or said second introgressed allele. In some embodiments, methods of the invention comprise selecting a progeny plant by detecting at least one polymorphism at a locus selected from the group consisting of marker locus M1 (SEQ ID NO:1), M2 (SEQ ID NO:6), M3 (SEQ ID NO:11), or M4 (SEQ ID NO:12).

Because genetically diverse plant lines can be difficult to cross, the introgression of Fol resistance alleles into cultivated lines using conventional breeding methods could require prohibitively large segregating populations for progeny screens with an uncertain outcome. Marker-assisted selection (MAS) is therefore essential for the effective introgression of Fol resistance alleles into elite cultivars. However, previously known markers for Fol resistance have failed to discriminate between donor DNA conferring disease resistance and donor DNA conferring deleterious traits. This has been further complicated by the previous inability to resolve the specific regions associated with disease resistance. For the first time, the present invention enables effective MAS by providing improved and validated markers for detecting genotypes associated with disease resistance without the need to grow large populations of plants to maturity in order to observe the phenotype.

I. GENOMIC REGIONS, ALLELES, AND POLYMORPHISMS ASSOCIATED WITH FOL RESISTANCE IN TOMATO PLANTS

The invention provides novel introgressions of one or more alleles associated with disease resistance and fruit quality in tomato plants, together with polymorphic nucleic acids and linked markers for tracking the introgressions during plant breeding.

Tomato lines exhibiting Fol resistance are known in the art and may be used together with the novel trait-linked markers provided herein in accordance with certain embodiments of the invention. For example, the wild tomato accession *Solanum pennellii* LA0716 (available from the Tomato Genetic Resource Center in Davis, Calif., USA), can be used as a source for I-3 resistance. However, the present inventors observed for the first time that introgressing Fol resistance from LA0716 into cultivated lines is associated with an agronomically unacceptable plant architecture including a deleterious soft fruit trait. This was further complicated by the discovery that the I-3 disease resistance trait and the soft fruit trait were found to be so tightly linked that the recombination event uncoupling the two traits occurs only every one in 10,000 plants, and that the markers that separate the two loci have the same genetic position.

Using the improved genetic markers and assays of the invention, Applicants were able to successfully identify novel Fol resistance regions associated with fewer deleterious traits when introgressed into a cultivated line. In certain embodiments, the invention provides tomato plants comprising donor DNA from a Fol resistant line between marker locus M2 (SEQ ID NO:6) and M3 (SEQ ID NO:11) on chromosome 7.

The novel introgressions provided herein confer robust resistance to Fol, while avoiding the reduction in fruit quality seen with conventional introgressions. The invention therefore represents a significant advance by providing novel introgressions conferring robust resistance to Fol without poor fruit quality.

II. INTROGRESSION OF GENOMIC REGIONS ASSOCIATED WITH DISEASE RESISTANCE

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a Fol resistant plant into a cultivated line. The invention further provides markers for identifying and tracking the novel introgressions disclosed herein during plant breeding, including the markers set forth in Table 1. Other embodiments of the invention provide marker M2 (SEQ ID NO:6), which has been shown to be genetically linked to Fol resistance in plants.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistant phenotype.

Tomato plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Tomato plants comprising an introgressed region comprising regions closely linked to or adjacent to the genomic regions and markers provided herein and associated with a disease resistance phenotype are also provided.

III. DEVELOPMENT OF DISEASE RESISTANT TOMATO VARIETIES

For most breeding objectives, commercial breeders work with germplasm that is "cultivated," "cultivated type," or "elite." These cultivated lines may be used as recurrent parents or as a source of recurrent parent alleles during breeding. Cultivated or elite germplasm is easier to breed because it generally performs well when evaluated for horticultural performance. Many cultivated tomato types have been developed and are known in the art as being agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. Non-cultivated germplasm may be used as a source of donor alleles during breeding. However, this approach generally presents significant difficulties due to fertility problems associated with crosses between diverse lines, and negative linkage drag from the non-cultivated parent. For example, non-cultivated tomato types can provide alleles associated with disease resistance. However, these non-cultivated types may have poor horticultural qualities such as poor quality or architecture.

The process of introgressing desirable resistance genes from non-cultivated lines into elite cultivated lines while avoiding problems with linkage drag or low heritability is a long and often arduous process. In deploying alleles derived from wild relatives it is often desirable to introduce a minimal or truncated introgression that provides the desired trait but lacks detrimental effects. To aid introgression reliable marker assays are preferable to phenotypic screens. Success is furthered by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, the inventors' discovery of accurate markers associated with disease resistance will facilitate the development of tomato plants having beneficial phenotypes. For example, seed can be genotyped using the markers of the present invention to select for plants comprising desired genomic regions associated with disease resistance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding traits that are genetically tightly linked. Therefore, in the absence of accurate markers, suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among tomato species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. MARKER ASSISTED BREEDING TECHNIQUES

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita, et al. (1989) Genomics, 8(2), 271-278), denaturing gradient gel electrophoresis (Myers (1985) EPO 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992)

*Biotechniques* 12(1), 82-87), or PCR amplification of multiple specific alleles (PAMSA; Dutton and Sommer (1991) *Biotechniques*, 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a tomato plant a genotype associated with disease resistance, identify a tomato plant with a genotype associated with disease resistance, and to select a tomato plant with a genotype associated with disease resistance. In certain embodiments of methods of the invention, polymorphic nucleic acids can be used to produce a tomato plant that comprises in its genome an introgressed locus associated with disease resistance. In certain embodiments of the invention, polymorphic nucleic acids can be used to breed progeny tomato plants comprising a locus or loci associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to a condition where the two alleles at a locus are different.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in tomato plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. (1986) Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to detect polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is described in U.S. Pat. Nos. 6,799,122; 6,913,879; and 6,996, 476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Some embodiments include methods for treating tomato, tomato plant parts, or the soil or substrate in which tomato plants are grown or intended to be grown with an active compound or a combination of active compounds. In some embodiments, the tomato plants are suspected of being infected or of becoming infected with a disease, or the methods are for protecting or treating plants from fungal and bacterial infections. In some embodiments the disease is a fungal infection, and the embodiments include methods for protecting from a fungal disease. In further embodiments, the tomato plant comprises a recombinant chromosomal segment on chromosome 7 that comprises a *Fusarium oxysporum* f sp. *lycopersici* (Fol) resistance allele. In some embodiments, said chromosomal segment lacks a deleterious allele that confers a soft fruit trait to said plant when present. In further embodiments, the treatment increases tomato yield. In some embodiments, the active compound or combination of active compounds comprises a fungicidal active ingredient. In certain embodiments, the active compound is selected from the following groups: (1) inhibitors of the ergosterol synthesis, (2) inhibitors of the respiratory chain at complex I or II, (3) inhibitors of the respiratory chain at complex III, (4) inhibitors of the mitosis and cell division, (5) compounds capable of having a multisite action, (6) compounds capable of inducing a host defense, (7) inhibitors of the amino acid and/or protein biosynthesis, (8) inhibitors of the ATP production, (9) inhibitors of the cell wall synthesis, (10) inhibitors of the lipid and membrane synthesis, (11) inhibitors of the melanine biosynthesis, (12) inhibitors of the nucleic acid synthesis, (13) inhibitors of the signal transduction, (14) compounds capable of acting as uncoupler, and (15) other fungicides. Examples of such active compounds, their synthesis, and analysis are provided in European Patent Application EP3335559A1.

In some embodiments, inhibitors of the ergosterol synthesis are selected from the group consisting of (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2 S, 5 S)-5-(4-chlorobenzyl)-2-(chloromethyl)-2-methyl-1-(1H-1,2,4-triazol-1-ylmethyl)cyclopentanol, (1.027) (1 S,2R,5R)-5-(4-chlorobenzyl)-2-(chloromethyl)-2-methyl-1-(1H-1,2,4-triazol-1-ylmethyl)-cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1 S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2 S)-2-(1-chlorocyclopropyl)-4-[(1R)-2,2-dichlorocyclopropyl]-1-(1H-1,2,4-triazol-1-yl)butan-2-ol, (1.032) (2 S)-2-(1-chlorocyclopropyl)-4-[(1 S)-2,2-dichlorocyclopropyl]-1-(1H-1,2,4-triazol-1-yl)butan-2-ol, (1.033) (2 S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-di fluorophenyl)-1,2-oxazol-4-yl](pyridin-3-yl)methanol, (1.036) [3-(4-chloro-2-fluorophenyl)-5-(2,4-di fluorophenyl)-1,2-oxazol-4-yl](pyridin-3-yl)methanol, (1.037) 1-({(2R,4 S)-2-[2-chloro-4-(4-chlorophenoxy)phenyl]-4-methyl-1,3-dioxolan-2-yl}methyl)-1H-1,2,4-triazole, (1.038) 1-({(2 S,4 S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3 S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5 S)-1-(2,4-dichlorophenyl)-5-hydroxy-2,6,6-trimethylheptan-4-yl]-2,4-dihydro-3H-1,2,4-triazole-3-thione, (1.044) 2-[(2R,4 S,5R)-1-(2,4-dichlorophenyl)-5-hydroxy-2,6,6-trimethylheptan-4-yl]-2, 4-dihydro-3H-1,2,4-triazole-3-thione, (1.045) 2-[(2R,4 S,5 S)-1-(2,4-dichlorophenyl)-5-hydroxy-2,6,6-trimethylheptan-4-yl]-2,4-dihydro-3H-1,2,4-triazole-3-thione, (1.046) 2-[(2 S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2 S,4R,5 S)-1-(2,4-dichlorophenyl)-5-hydroxy-2,6,6-trimethylheptan-4-yl]-2,4-dihydro-3H-1,2,4-triazole-3-thione, (1.048) 2-[(2 S,4 S,5R)-1-(2,4-dichlorophenyl)-5-hydroxy-2,6,6-trimethylheptan-4-yl]-2, 4-dihydro-3H-1,2,4-triazole-3-thione, (1.049) 2-[(2 S,4 S,5 S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-di chlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl-2,4}-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3 S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran- 2-yl]methyl}-1H-1,2,4-triazole, (1.062) 5-(allylsulfanyl)-1-{[rel(2R,3 S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N— methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-di chloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1 S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Mefentrifluconazole, and (1.082) Ipfentrifluconazole.

In some embodiments, inhibitors of the respiratory chain at complex I or II are selected from the group consisting of (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4 S,9 S), (2.011) isopyrazam (anti-epimeric enantiomer 1 S,4R,9R), (2.012) isopyrazam (anti-epimeric racemate 1RS,4 SR,9 SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4 S,9R), (2.015) isopyrazam (syn-epimeric enantiomer 1 S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3 S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3 S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3 S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4 S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1 S,4R)-9-(di chloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, and (2.056) N-cyclopropyl-N-(2-cyclopropylbenzyl)-3-(difluoromethyl)-5-fluoro-1-methyl-1H-pyrazole-4-carboxamide.

In some embodiments, inhibitors of the respiratory chain at complex III are selected from the group consisting of (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[(1[(1E)-1-(3-{[(E)-1-fluoro-2-phenylvinyl]oxy}phenypethylidene]amino oxy)methyl]phenyl}-2-(methoxyimino)-N-methyl acetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methyl acetamide, (3.024) (2 S)-2-{2-[(2,5-dimethylphenoxy)methyl]phenyl}-2-methoxy-N-methyl acetamide, (3.025) (3 S,6 S, 7R, 8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methyl acetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, and (3.029) methyl {5-[3-(2,4-dimethylphenyl)-1H-pyrazol-1-yl]-2-methylbenzyl}carbamate.

In some embodiments, inhibitors of the mitosis and cell division are selected from the group consisting of (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-di methyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, and (4.025) N-(4-chloro-2,6-difluorophenyl)-4-(2-chloro-4-fluorophenyl)-1,3-dimethyl-1H-pyrazol-5-amine.

In some embodiments, compounds capable of having a multisite action are selected from the group consisting of (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, and (5.023) 6-ethyl-5,7-dioxo-6,7-dihydro-5H-pyrrolo[3',4':5,6][1,4]dithiino[2,3-c][1,2]thiazole-3-carbonitrile.

In some embodiments, compounds capable of inducing a host defense are selected from the group consisting of (6.001) acibenzolar-S-methyl, (6.002) isotianil, (6.003) probenazole, and (6.004) tiadinil.

In some embodiments, inhibitors of the amino acid and/or protein biosynthesis are selected from the group consisting of (7.001) cyprodinil, (7.002) kasugamycin, (7.003) kasugamycin hydrochloride hydrate, (7.004) oxytetracycline, (7.005) pyrimethanil, and (7.006) 3-(5-fluoro-3,3,4,4-tetramethyl-3,4-dihydroisoquinolin-1-yl)quinolone.

In some embodiments, inhibitor of the ATP production is selected from the group consisting of (8.001) silthiofam.

In some embodiments, inhibitors of the cell wall synthesis are selected from the group consisting of (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, and (9.009) (2Z)-3-(4-tert-butylphenyl)-3-(2-chloropyridin-4-yl)-1-(morpholin-4-yl)prop-2-en-1-one.

In some embodiments, inhibitors of the lipid and membrane synthesis are selected from the group consisting of (10.001) propamocarb, (10.002) propamocarb hydrochloride, and (10.003) tolclofos-methyl.

In some embodiments, inhibitors of the melanine biosynthesis are selected from the group consisting of (11.001) tricyclazole, and (11.002) 2,2,2-trifluoroethyl {3-methyl-1-[(4-methylbenzoyl)amino]butan-2-yl}carbamate.

In some embodiments, inhibitors of the nucleic acid synthesis are selected from the group consisting of (12.001) benalaxyl, (12.002) benalaxyl-M (kiralaxyl), (12.003) metalaxyl, and (12.004) metalaxyl-M (mefenoxam).

In some embodiments, inhibitors of the signal transduction are selected from the group consisting of (13.001) fludioxonil, (13.002) iprodione, (13.003) procymidone, (13.004) proquinazid, (13.005) quinoxyfen, and (13.006) vinclozolin.

In some embodiments, compounds capable of acting as uncoupler are selected from the group consisting of (14.001) fluazinam, and (14.002) meptyldinocap.

In some embodiments, other fungicides are selected from the group consisting of (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyl dithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5 S)-5-(2,6-difluorophenyl)-4,5- dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl] ethanone, (15.036) 2-[3,5-bis(difluoromethyl)-1H-pyrazol-1-yl]-1-[4-(4-{5-[2-chloro-6-(prop-2-yn-1-yl oxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yl oxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene] amino}oxy)methyl]pyridin-2-yl}carbamate, and (15.062) 5-fluoro-4-imino-3-methyl-1-[(4-m ethylphenyl)sulfonyl]-3,4-dihydropyrimidin-2(1H)-one.

In certain embodiments, the active compound or combination of active compounds is selected from:

(1.001) cyproconazole, (1.002) difenoconazole, (1.003) epoxiconazole, (1.004) fenhexamid, (1.010) imazalil, (1.012) ipconazole, (1.013) metconazole, (1.017) propiconazole, (1.018) prothioconazole, (1.020) spiroxamine, (1.021) tebuconazole, (1.026) (1R,2 S,5 S)-5-(4-chlorobenzyl)-2-(chloromethyl)-2-methyl-1-(1H-1,2,4-triazol-1-ylmethyl)cyclopentanol, (1.027) (1 S,2R,5R)-5-(4-chlorobenzyl)-2-(chloromethyl)-2-methyl-1-(1H-1,2,4-triazol-1-ylmethyl)cyclopentanol, (1.059) 5-(4-chlorobenzyl)-2-(chloromethyl)-2-methyl-1-(1H-1,2,4-triazol-1-ylmethyl)cyclopentanol, (1.081) Mefentrifluconazole, and (1.082) Ipfentrifluconazole, (2.001) benzovindiflupyr, (2.002) bixafen, (2.003) boscalid, (2.005) fluopyram, (2.007) fluxapyroxad, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR, 9RS), (2.017) penflufen, (2.018) penthiopyrad, (2.019) pydiflumetofen, (2.021) sedaxane, (2.027) 3-(difluoromethyl)-1-methyl-N-(1,1,3-trimethyl-2,3-dihydro-1H-inden-4-yl)-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (3.003) azoxystrobin, (3.007) dimoxystrobin, (3.012) fluoxastrobin, (3.013) kresoxim-methyl, (3.016) picoxystrobin, (3.017) pyraclostrobin, (3.020) trifloxystrobin, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methyl acetamide, (4.005) pencycuron, (4.007) thiophanate-methyl, (4.012) 4-(2-bromo-4-fluorophenyl)-N-(2,6-di fluorophenyl)-1,3-di methyl-1H-pyrazol-5-amine, (4.015) 4-(2-bromo-4-fluorophenyl)-N-(2-chloro-6-fluorophenyl)-1,3-di methyl-1H-pyrazol-5-amine, (4.025) N-(4-chloro-2,6-di fluorophenyl)-4-(2-chloro-4-fluorophenyl)-1,3-di methyl-1H-pyrazol-5-amine, (5.003) captan, (5.004) chlorothalonil, (5.011) dodine, (5.012) folpet, (5.013) mancozeb, (5.015) metiram, (5.018) propineb, (6.002) isotianil, (7.001) cyprodinil, (7.005) pyrimethanil, (12.003) metalaxyl, (12.004) metalaxyl-M (mefenoxam), (13.001) fludioxonil, (13.002) iprodione, (13.004) proquinazid, (13.005) quinoxyfen, (14.001) fluazinam, (14.002) meptyldinocap, (15.008) cyflufenamid, (15.010) cyprosulfamide, (15.011) flutianil, (15.012) fosetyl-aluminium, (15.016) metrafenone, (15.027) pyriofenone (chlazafenone), and (15.047) 3-(4,4-difluoro-3,3-dimethyl-3,4-dihydroisoquinolin-1-yl)quinolone, (15.048) 4-amino-5-fluoropyrimidin-2-ol (tautomeric form: 4-amino-5-fluoropyrimidin-2(1H)-one), (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.062) 5-fluoro-4-imino-3-methyl-1-[(4-methylphenyl)sulfonyl]-3,4-dihydropyrimidin-2(1H)-one.

In certain embodiments, the active compound or combination of active compounds is selected from:

(1.002) difenoconazole, (1.010) imazalil, (1.012) ipconazole, (1.018) prothioconazole, (1.020) spiroxamine, (1.021) tebuconazole, (1.026) (1R,2S,5 S)-5-(4-chlorobenzyl)-2-(chloromethyl)-2-methyl-1-(1H-1,2,4-triazol-1-ylmethyl)cyclopentanol, (1.027) (1 S,2R,5R)-5-(4-chlorobenzyl)-2-(chloromethyl)-2-methyl-1-(1H-1,2,4-triazol-1-ylmethyl)cyclopentanol, (1.059) 5-(4-chlorobenzyl)-2-(chloromethyl)-2-methyl-1-(1H-1,2, 4-triazol-1-ylmethyl)cyclopentanol, (1.081) Mefentrifluconazole, and (1.082) Ipfentrifluconazole, (2.001) benzovindiflupyr, (2.002) bixafen, (2.005) fluopyram, (2.007) fluxapyroxad, (2.017) penflufen, (2.018) penthiopyrad, (2.019) pydiflumetofen, (2.021) sedaxane, (2.027) 3-(difluoromethyl)-1-methyl-N-(1,1,3-trimethyl-2,3-dihydro-1H-inden-4-yl)-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (3.003) azoxystrobin, (3.012) fluoxastrobin, (3.016) picoxystrobin, (3.017) pyraclostrobin, (3.020) trifloxystrobin, (3.025) (3 S,6S,7R,8R)-8-benzyl-3-[({3-[(isobutyryl oxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methyl acetamide, (4.005) pencycuron, (4.007) thiophanate-methyl, (4.012) 4-(2-bromo-4-fluorophenyl)-N-(2,6-di fluorophenyl)-1,3-di methyl-1H-pyrazol-5-amine, (4.015) 4-(2-bromo-4-fluorophenyl)-N-(2-chloro-6-fluorophenyl)-1,3-di methyl-1H-pyrazol-5-amine, (4.025) N-(4-chloro-2,6-di fluorophenyl)-4-(2-chloro-4-fluorophenyl)-1,3-dimethyl-1H-pyrazol-5-amine, (5.004) chlorothalonil, (5.011) dodine, (5.012) folpet, (5.013) mancozeb, (5.018) propineb, (6.002) isotianil, (7.005) pyrimethanil, (12.003) metalaxyl, (12.004) metalaxyl-M (mefenoxam), (13.001) fludioxonil, (13.004) proquinazid, (14.001) fluazinam, (14.002) meptyldinocap, (15.008) cyflufenamid, (15.027) pyriofenone (chlazafenone), (15.047) 3-(4,4-difluoro-3,3-dimethyl-3,4-dihydroisoquinolin-1-yl)quinolone, (15.048) 4-amino-5-fluoropyrimidin-2-ol (tautomeric form: 4-amino-5-fluoropyrimidin-2(1H)-one), (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.062) 5-fluoro-4-imino-3-methyl-1-[(4-methylphenyl)sulfonyl]-3,4-dihydropyrimidin-2(1H)-one.

In certain embodiments, the active compound or combination of active compounds is selected from:

(1.012) ipconazole, (1.018) prothioconazole, (1.020) spiroxamine, (1.021) tebuconazole, (2.002) bixafen, (2.005) fluopyram, (2.017) penflufen, (2.027) 3-(difluoromethyl)-1-methyl-N-(1,1,3-trimethyl-2,3-dihydro-1H-inden-4-yl)-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (3.020) trifloxystrobin, (3.025) (3 S,6 S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (4.005) pencycuron, (5.004) chlorothalonil, (5.013) mancozeb, (5.018) propineb, (12.003) metalaxyl, (12.004) metalaxyl-M (mefenoxam), (13.001) fludioxonil, (13.004) proquinazid, (15.008) cyflufenamid, and (15.047) 3-(4,4-difluoro-3,3-dimethyl-3,4-dihydroisoquinolin-1-yl)quinoline.

In certain embodiments, the active compound or combination of active compounds are selected from the group (G1) consisting of the following mixtures: (I.01)+(1.001), (I.01)+(1.002), (I.01)+(1.003), (I.01)+(1.004), (I.01)+(1.005), (I.01)+(1.006), (I.01)+(1.007), (I.01)+(1.008), (I.01)+(1.009), (I.01)+(1.010), (I.01)+(1.011), (I.01)+(1.012), (I.01)+(1.013), (I.01)+(1.014), (I.01)+(1.015), (I.01)+(1.016), (I.01)+(1.017), (I.01)+(1.018), (I.01)+(1.019), (I.01)+(1.020), (I.01)+(1.021), (I.01)+(1.022), (I.01)+(1.023), (I.01)+(1.024), (I.01)+(1.025), (I.01)+(1.026), (I.01)+(1.027), (I.01)+(1.028), (I.01)+(1.029), (I.01)+(1.030), (I.01)+(1.031), (I.01)+(1.032), (I.01)+(1.033), (I.01)+(1.034), (I.01)+(1.035), (I.01)+(1.036), (I.01)+(1.037), (I.01)+(1.038), (I.01)+(1.039), (I.01)+(1.040), (I.01)+(1.041), (I.01)+(1.042), (I.01)+(1.043), (I.01)+(1.044), (I.01)+(1.045), (I.01)+(1.046), (I.01)+(1.047), (I.01)+(1.048), (I.01)+(1.049), (I.01)+(1.050), (I.01)+(1.051), (I.01)+(1.052), (I.01)+(1.053), (I.01)+(1.054), (I.01)+(1.055), (I.01)+(1.056), (I.01)+(1.057), (I.01)+(1.058), (I.01)+(1.059), (I.01)+(1.060), (I.01)+(1.061), (I.01)+(1.062), (I.01)+(1.063), (I.01)+(1.064), (I.01)+(1.065), (I.01)+(1.066), (I.01)+(1.067), (I.01)+(1.068), (I.01)+(1.069), (I.01)+(1.070), (I.01)+(1.071), (I.01)+(1.072), (I.01)+(1.073), (I.01)+(1.074), (I.01)+(1.075), (I.01)+(1.076), (I.01)+(1.077), (I.01)+(1.078), (I.01)+(1.079), (I.01)+(1.080), (I.01)+(1.081), (I.01)+(1.082), (I.01)+(2.001), (I.01)+(2.002), (I.01)+(2.003), (I.01)+(2.004), (I.01)+(2.005), (I.01)+(2.006), (I.01)+(2.007), (I.01)+(2.008), (I.01)+(2.009), (I.01)+(2.010), (I.01)+(2.011), (I.01)+(2.012), (I.01)+(2.013), (I.01)+(2.014), (I.01)+(2.015), (I.01)+(2.016), (I.01)+(2.017), (I.01)+(2.018), (I.01)+(2.019), (I.01)+(2.020), (I.01)+(2.021), (I.01)+(2.022), (I.01)+(2.023), (I.01)+(2.024), (I.01)+(2.025), (I.01)+(2.026), (I.01)+(2.027), (I.01)+(2.028), (I.01)+(2.029), (I.01)+(2.030), (I.01)+(2.031), (I.01)+(2.032), (I.01)+(2.033), (I.01)+(2.034), (I.01)+(2.035), (I.01)+(2.036), (I.01)+(2.037), (I.01)+(2.038), (I.01)+(2.039), (I.01)+(2.040), (I.01)+(2.041), (I.01)+(2.042), (I.01)+(2.043), (I.01)+(2.044), (I.01)+(2.045), (I.01)+(2.046), (I.01)+(2.047), (I.01)+(2.048), (I.01)+(2.049), (I.01)+(2.050), (I.01)+(2.051), (I.01)+(2.052), (I.01)+(2.053), (I.01)+(2.054), (I.01)+(2.055), (I.01)+(2.056), (I.01)+(3.001), (I.01)+(3.002), (I.01)+(3.003), (I.01)+(3.004), (I.01)+(3.005), (I.01)+(3.006), (I.01)+(3.007), (I.01)+(3.008), (I.01)+(3.009), (I.01)+(3.010), (I.01)+(3.011), (I.01)+(3.012), (I.01)+(3.013), (I.01)+(3.014), (I.01)+(3.015), (I.01)+(3.016), (I.01)+(3.017), (I.01)+(3.018), (I.01)+(3.019), (I.01)+(3.020), (I.01)+(3.021), (I.01)+(3.022), (I.01)+(3.023), (I.01)+(3.024), (I.01)+(3.025), (I.01)+(3.026), (I.01)+(3.027), (I.01)+(3.028), (I.01)+(3.029), (I.01)+(4.001), (I.01)+(4.002), (I.01)+(4.003), (I.01)+(4.004), (I.01)+(4.005), (I.01)+(4.006), (I.01)+(4.007), (I.01)+(4.008), (I.01)+(4.009), (I.01)+(4.010), (I.01)+(4.011), (I.01)+(4.012), (I.01)+(4.013), (I.01)+(4.014), (I.01)+(4.015), (I.01)+(4.016), (I.01)+(4.017), (I.01)+(4.018), (I.01)+(4.019), (I.01)+(4.020), (I.01)+(4.021), (I.01)+(4.022), (I.01)+(4.023), (I.01)+(4.024), (I.01)+(4.025), (I.01)+(5.001), (I.01)+(5.002), (I.01)+(5.003), (I.01)+(5.004), (I.01)+(5.005), (I.01)+(5.006), (I.01)+(5.007), (I.01)+(5.008), (I.01)+(5.009), (I.01)+(5.010), (I.01)+(5.011), (I.01)+(5.012), (I.01)+(5.013), (I.01)+(5.014), (I.01)+(5.015), (I.01)+(5.016), (I.01)+(5.017), (I.01)+(5.018), (I.01)+(5.019), (I.01)+(5.020), (I.01)+(5.021), (I.01)+(5.022), (I.01)+(5.023), (I.01)+(6.001), (I.01)+(6.002), (I.01)+(6.003), (I.01)+(6.004), (I.01)+(7.001), (I.01)+(7.002), (I.01)+(7.003), (I.01)+(7.004), (I.01)+(7.005), (I.01)+(7.006), (I.01)+(8.001), (I.01)+(9.001), (I.01)+(9.002), (I.01)+(9.003), (I.01)+(9.004), (I.01)+(9.005), (I.01)+(9.006), (I.01)+(9.007), (I.01)+(9.008), (I.01)+(9.009), (I.01)+(10.001), (I.01)+(10.002), (I.01)+(10.003), (I.01)+(11.001), (I.01)+(11.002), (I.01)+(12.001), (I.01)+(12.002), (I.01)+(12.003), (I.01)+(12.004), (I.01)+(13.001), (I.01)+(13.002), (I.01)+(13.003), (I.01)+(13.004), (I.01)+(13.005), (I.01)+(13.006), (I.01)+(14.001), (I.01)+(14.002), (I.01)+(15.001), (I.01)+(15.002), (I.01)+(15.003), (I.01)+(15.004), (I.01)+(15.005), (I.01)+(15.006), (I.01)+(15.007), (I.01)+(15.008), (I.01)+(15.009), (I.01)+(15.010), (I.01)±(15.011), (I.01)±(15.012), (I.01)+(15.013), (I.01)+(15.014), (I.01)+(15.015), (I.01)+(15.016), (I.01)+(15.017), (I.01)+(15.018), (I.01)+(15.019), (I.01)+(15.020), (I.01)+(15.021), (I.01)+(15.022), (I.01)+(15.023), (I.01)+(15.024), (I.01)+(15.025), (I.01)+(15.026), (I.01)+(15.027), (I.01)+(15.028), (I.01)+(15.029), (I.01)+(15.030), (I.01)+(15.031), (I.01)+(15.032), (I.01)+(15.033), (I.01)+(15.034), (I.01)+(15.035), (I.01)+(15.036), (I.01)+(15.037), (I.01)+(15.038), (I.01)+(15.039), (I.01)+(15.040), (I.01)+(15.041), (I.01)+(15.042), (I.01)+(15.043), (I.01)+(15.044), (I.01)+(15.045), (I.01)+(15.046), (I.01)+(15.047), (I.01)+(15.048), (I.01)+(15.049), (I.01)+(15.050), (I.01)+(15.051), (I.01)+(15.052), (I.01)+(15.053), (I.01)+(15.054), (I.01)+(15.055), (I.01)+(15.056), (I.01)+(15.057), (I.01)+(15.058), (I.01)+(15.059), (I.01)+(15.060), (I.01)+(15.061), and (I.01)+(15.062).

In certain embodiments, the active compound or combination of active compounds are selected from the group (G2) consisting of the following mixtures: (I.59)+(1.001), (I.59)+(1.002), (I.59)+(1.003), (I.59)+(1.004), (I.59)+(1.005), (I.59)+(1.006), (I.59)+(1.007), (I.59)+(1.008), (I.59)+(1.009), (I.59)+(1.010), (I.59)+(1.011), (I.59)+(1.012), (I.59)+(1.013), (I.59)+(1.014), (I.59)+(1.015), (I.59)+(1.016), (I.59)+(1.017), (I.59)+(1.018), (I.59)+(1.019), (I.59)+(1.020), (I.59)+(1.021), (I.59)+(1.022), (I.59)+(1.023), (I.59)+(1.024), (I.59)+(1.025), (I.59)+(1.026), (I.59)+(1.027), (I.59)+(1.028), (I.59)+(1.029), (I.59)+(1.030), (I.59)+(1.031), (I.59)+(1.032), (I.59)+(1.033), (I.59)+(1.034), (I.59)+(1.035), (I.59)+(1.036), (I.59)+(1.037), (I.59)+(1.038), (I.59)+(1.039), (I.59)+(1.040), (I.59)+(1.041), (I.59)+(1.042), (I.59)+(1.043), (I.59)+(1.044), (I.59)+(1.045), (I.59)+(1.046), (I.59)+(1.047), (I.59)+(1.048), (I.59)+(1.049), (I.59)+(1.050), (I.59)+(1.051), (I.59)+(1.052), (I.59)+(1.053), (I.59)+(1.054), (I.59)+(1.055), (I.59)+(1.056), (I.59)+(1.057), (I.59)+(1.058), (I.59)+(1.059), (I.59)+(1.060), (I.59)+(1.061), (I.59)+(1.062), (I.59)+(1.063), (I.59)+(1.064), (I.59)+(1.065), (I.59)+(1.066), (I.59)+(1.067), (I.59)+(1.068), (I.59)+(1.069), (I.59)+(1.070), (I.59)+(1.071), (I.59)+(1.072), (I.59)+(1.073), (I.59)+(1.074), (I.59)+(1.075), (I.59)+(1.076), (I.59)+(1.077), (I.59)+(1.078), (I.59)+(1.079), (I.59)+(1.080), (I.59)+(1.081), (I.59)+(1.082), (I.59)+(2.001), (I.59)+(2.002), (I.59)+(2.003), (I.59)+(2.004), (I.59)+(2.005), (I.59)+(2.006), (I.59)+(2.007), (I.59)+(2.008), (I.59)+(2.009), (I.59)+(2.010), (I.59)+(2.011), (I.59)+(2.012), (I.59)+(2.013), (I.59)+(2.014), (I.59)+(2.015), (I.59)+(2.016), (I.59)+(2.017), (I.59)+(2.018), (I.59)+(2.019), (I.59)+(2.020), (I.59)+(2.021), (I.59)+(2.022), (I.59)+(2.023), (I.59)+(2.024), (I.59)+(2.025), (I.59)+(2.026), (I.59)+(2.027), (I.59)+(2.028), (I.59)+(2.029), (I.59)+(2.030), (I.59)+(2.031), (I.59)+(2.032), (I.59)+(2.033), (I.59)+(2.034), (I.59)+(2.035), (I.59)+(2.036), (I.59)+(2.037), (I.59)+(2.038), (I.59)+(2.039), (I.59)+(2.040), (I.59)+(2.041), (I.59)+(2.042), (I.59)+(2.043), (I.59)+(2.044), (I.59)+(2.045), (I.59)+(2.046), (I.59)+(2.047), (I.59)+(2.048), (I.59)+(2.049), (I.59)+(2.050), (I.59)+(2.051), (I.59)+(2.052), (I.59)+(2.053), (I.59)+(2.054), (I.59)+(2.055), (I.59)+(2.056), (I.59)+(3.001), (I.59)+(3.002), (I.59)+(3.003), (I.59)+(3.004), (I.59)+(3.005), (I.59)+(3.006), (I.59)+(3.007), (I.59)+(3.008), (I.59)+(3.009), (I.59)+(3.010), (I.59)+(3.011), (I.59)+(3.012), (I.59)+(3.013), (I.59)+(3.014), (I.59)+(3.015), (I.59)+(3.016), (I.59)+(3.017), (I.59)+(3.018), (I.59)+(3.019), (I.59)+(3.020), (I.59)+(3.021), (I.59)+(3.022), (I.59)+(3.023), (I.59)+(3.024), (I.59)+(3.025), (I.59)+(3.026), (I.59)+(3.027), (I.59)+(3.028), (I.59)+(3.029), (I.59)+(4.001), (I.59)+(4.002), (I.59)+(4.003), (I.59)+(4.004), (I.59)+(4.005), (I.59)+(4.006), (I.59)+(4.007), (I.59)+(4.008), (I.59)+(4.009), (I.59)+(4.010), (I.59)+(4.011), (I.59)+(4.012), (I.59)+(4.013), (I.59)+(4.014), (I.59)+(4.015), (I.59)+(4.016), (I.59)+(4.017), (I.59)+(4.018), (I.59)+(4.019), (I.59)+(4.020), (I.59)+(4.021), (I.59)+(4.022), (I.59)+(4.023), (I.59)+(4.024), (I.59)+(4.025), (I.59)+(5.001), (I.59)+(5.002), (I.59)+(5.003), (I.59)+(5.004), (I.59)+(5.005), (I.59)+(5.006), (I.59)+(5.007), (I.59)+(5.008), (I.59)+(5.009), (I.59)+(5.010), (I.59)+(5.011), (I.59)+(5.012), (I.59)+(5.013), (I.59)+(5.014), (I.59)+(5.015), (I.59)+(5.016), (I.59)+(5.017), (I.59)+(5.018), (I.59)+(5.019), (I.59)+(5.020), (I.59)+(5.021), (I.59)+(5.022), (I.59)+(5.023), (I.59)+(6.001), (I.59)+(6.002), (I.59)+(6.003), (I.59)+(6.004), (I.59)+(7.001), (I.59)+(7.002), (I.59)+(7.003), (I.59)+(7.004), (I.59)+(7.005), (I.59)+(7.006), (I.59)+(8.001), (I.59)+(9.001), (I.59)+(9.002), (I.59)+(9.003), (I.59)+(9.004), (I.59)+(9.005), (I.59)+(9.006), (I.59)+(9.007), (I.59)+(9.008), (I.59)+(9.009), (I.59)+(10.001), (I.59)+(10.002), (I.59)+(10.003), (I.59)+(11.001), (I.59)+(11.002), (I.59)+(12.001), (I.59)+(12.002), (I.59)+(12.003), (I.59)+(12.004), (I.59)+(13.001), (I.59)+(13.002), (I.59)+(13.003), (I.59)+(13.004), (I.59)+(13.005), (I.59)+(13.006), (I.59)+(14.001), (I.59)+(14.002), (I.59)+(15.001), (I.59)+(15.002), (I.59)+(15.003), (I.59)+(15.004), (I.59)+(15.005), (I.59)+(15.006), (I.59)+(15.007), (I.59)+(15.008), (I.59)+(15.009), (I.59)+(15.010), (I.59)+(15.011), (I.59)+(15.012), (I.59)+(15.013), (I.59)+(15.014), (I.59)+(15.015), (I.59)+(15.016), (I.59)+(15.017), (I.59)+(15.018), (I.59)+(15.019), (I.59)+(15.020), (I.59)+(15.021), (I.59)+(15.022), (I.59)+(15.023), (I.59)+(15.024), (I.59)+(15.025), (I.59)+(15.026), (I.59)+(15.027), (I.59)+(15.028), (I.59)+(15.029), (I.59)+(15.030), (I.59)+(15.031), (I.59)+(15.032), (I.59)+(15.033), (I.59)+(15.034), (I.59)+(15.035), (I.59)+(15.036), (I.59)+(15.037), (I.59)+(15.038), (I.59)+(15.039), (I.59)+(15.040), (I.59)+(15.041), (I.59)+(15.042), (I.59)+(15.043), (I.59)+(15.044), (I.59)+(15.045), (I.59)+(15.046), (I.59)+(15.047), (I.59)+(15.048), (I.59)+(15.049), (I.59)+(15.050), (I.59)+(15.051), (I.59)+(15.052), (I.59)+(15.053), (I.59)+(15.054), (I.59)+(15.055), (I.59)+(15.056), (I.59)+(15.057), (I.59)+(15.058), (I.59)+(15.059), (I.59)+(15.060), (I.59)+(15.061), and (I.59)+(15.062).

In certain embodiments, the active compound or combination of active compounds are selected from the group (G3) consisting of the following mixtures: (I.81)+(1.001), (I.81)+(1.002), (I.81)+(1.003), (I.81)+(1.004), (I.81)+(1.005), (I.81)+(1.006), (I.81)+(1.007), (I.81)+(1.008), (I.81)+(1.009), (I.81)+(1.010), (I.81)+(1.011), (I.81)+(1.012), (I.81)+(1.013), (I.81)+(1.014), (I.81)+(1.015), (I.81)+(1.016), (I.81)+(1.017), (I.81)+(1.018), (I.81)+(1.019), (I.81)+(1.020), (I.81)+(1.021), (I.81)+(1.022), (I.81)+(1.023), (I.81)+(1.024), (I.81)+(1.025), (I.81)+(1.026), (I.81)+(1.027), (I.81)+(1.028), (I.81)+(1.029), (I.81)+(1.030), (I.81)+(1.031), (I.81)+(1.032), (I.81)+(1.033), (I.81)+(1.034), (I.81)+(1.035), (I.81)+(1.036), (I.81)+(1.037), (I.81)+(1.038), (I.81)+(1.039), (I.81)+(1.040), (I.81)+(1.041), (I.81)+(1.042), (I.81)+(1.043), (I.81)+(1.044), (I.81)+(1.045), (I.81)+(1.046), (I.81)+(1.047), (I.81)+(1.048), (I.81)+(1.049), (I.81)+(1.050), (I.81)+(1.051), (I.81)+(1.052), (I.81)+(1.053), (I.81)+(1.054), (I.81)+(1.055), (I.81)+(1.056), (I.81)+(1.057), (I.81)+(1.058), (I.81)+(1.059), (I.81)+(1.060), (I.81)+(1.061), (I.81)+(1.062), (I.81)+(1.063), (I.81)+(1.064), (I.81)+(1.065), (I.81)+(1.066), (I.81)+(1.067), (I.81)+(1.068), (I.81)+(1.069), (I.81)+(1.070), (I.81)+(1.071), (I.81)+(1.072), (I.81)+(1.073), (I.81)+(1.074), (I.81)+(1.075), (I.81)+(1.076), (I.81)+(1.077), (I.81)+(1.078), (I.81)+(1.079), (I.81)+(1.080), (I.81)+(1.081), (I.81)+(1.082), (I.81)+(2.001), (I.81)+(2.002), (I.81)+(2.003), (I.81)+(2.004), (I.81)+(2.005), (I.81)+(2.006), (I.81)+(2.007), (I.81)+(2.008), (I.81)+(2.009), (I.81)+(2.010), (I.81)+(2.011), (I.81)+(2.012), (I.81)+(2.013), (I.81)+(2.014), (I.81)+(2.015), (I.81)+(2.016), (I.81)+(2.017), (I.81)+(2.018), (I.81)+(2.019), (I.81)+(2.020), (I.81)+(2.021), (I.81)+(2.022), (I.81)+(2.023), (I.81)+(2.024), (I.81)+(2.025), (I.81)+(2.026), (I.81)+(2.027), (I.81)+(2.028), (I.81)+(2.029), (I.81)+(2.030), (I.81)+(2.031), (I.81)+(2.032), (I.81)+(2.033), (I.81)+(2.034), (I.81)+(2.035), (I.81)+(2.036), (I.81)+(2.037), (I.81)+(2.038), (I.81)+(2.039), (I.81)+(2.040), (I.81)+(2.041), (I.81)+(2.042), (I.81)+(2.043), (I.81)+(2.044), (I.81)+(2.045), (I.81)+(2.046), (I.81)+(2.047), (I.81)+(2.048), (I.81)+(2.049), (I.81)+(2.050), (I.81)+(2.051), (I.81)+(2.052), (I.81)+(2.053), (I.81)+(2.054), (I.81)+(2.055), (I.81)+(2.056), (I.81)+(3.001), (I.81)+(3.002), (I.81)+(3.003), (I.81)+(3.004), (I.81)+(3.005), (I.81)+(3.006), (I.81)+(3.007), (I.81)+(3.008), (I.81)+(3.009), (I.81)+(3.010), (I.81)+(3.011), (I.81)+(3.012), (I.81)+(3.013), (I.81)+(3.014), (I.81)+(3.015), (I.81)+(3.016), (I.81)+(3.017), (I.81)+(3.018), (I.81)+(3.019), (I.81)+(3.020), (I.81)+(3.021), (I.81)+(3.022), (I.81)+(3.023), (I.81)+(3.024), (I.81)+(3.025), (I.81)+(3.026), (I.81)+(3.027), (I.81)+(3.028), (I.81)+(3.029), (I.81)+(4.001), (I.81)+(4.002), (I.81)+(4.003), (I.81)+(4.004), (I.81)+(4.005), (I.81)+(4.006), (I.81)+(4.007), (I.81)+(4.008), (I.81)+(4.009), (I.81)+(4.010), (I.81)+(4.011), (I.81)+(4.012), (I.81)+(4.013), (I.81)+(4.014), (I.81)+(4.015), (I.81)+(4.016), (I.81)+(4.017), (I.81)+(4.018), (I.81)+(4.019), (I.81)+(4.020), (I.81)+(4.021), (I.81)+(4.022), (I.81)+(4.023), (I.81)+(4.024), (I.81)+(4.025), (I.81)+(5.001), (I.81)+(5.002), (I.81)+(5.003), (I.81)+(5.004), (I.81)+(5.005), (I.81)+(5.006), (I.81)+(5.007), (I.81)+(5.008), (I.81)+(5.009), (I.81)+(5.010), (I.81)+(5.011), (I.81)+(5.012), (I.81)+(5.013), (I.81)+(5.014), (I.81)+(5.015), (I.81)+(5.016), (I.81)+(5.017), (I.81)+(5.018), (I.81)+(5.019), (I.81)+(5.020), (I.81)+(5.021), (I.81)+(5.022), (I.81)+(5.023), (I.81)+(6.001), (I.81)+(6.002), (I.81)+(6.003), (I.81)+(6.004), (I.81)+(7.001), (I.81)+(7.002), (I.81)+(7.003), (I.81)+(7.004), (I.81)+(7.005), (I.81)+(7.006), (I.81)+(8.001), (I.81)+(9.001), (I.81)+(9.002), (I.81)+(9.003), (I.81)+(9.004), (I.81)+(9.005), (I.81)+(9.006), (I.81)+(9.007), (I.81)+(9.008), (I.81)+(9.009), (I.81)+(10.001), (I.81)+(10.002), (I.81)+(10.003), (I.81)+(11.001), (I.81)+(11.002), (I.81)+(12.001), (I.81)+(12.002), (I.81)+(12.003), (I.81)+(12.004), (I.81)+(13.001), (I.81)+(13.002), (I.81)+(13.003), (I.81)+(13.004), (I.81)+(13.005), (I.81)+(13.006), (I.81)+(14.001), (I.81)+(14.002), (I.81)+(15.001), (I.81)+(15.002), (I.81)+(15.003), (I.81)+(15.004), (I.81)+(15.005), (I.81)+(15.006), (I.81)+(15.007), (I.81)+(15.008), (I.81)+(15.009), (I.81)+(15.010), (I.81)+(15.011), (I.81)+(15.012), (I.81)+(15.013), (I.81)+(15.014), (I.81)+(15.015), (I.81)+(15.016), (I.81)+(15.017), (I.81)+(15.018), (I.81)+(15.019), (I.81)+(15.020), (I.81)+(15.021), (I.81)+(15.022), (I.81)+(15.023), (I.81)+(15.024), (I.81)+(15.025), (I.81)+(15.026), (I.81)+(15.027), (I.81)+(15.028), (I.81)+(15.029), (I.81)+(15.030), (I.81)+(15.031), (I.81)+(15.032), (I.81)+(15.033), (I.81)+(15.034), (I.81)+(15.035), (I.81)+(15.036), (I.81)+(15.037), (I.81)+(15.038), (I.81)+(15.039), (I.81)+(15.040), (I.81)+(15.041), (I.81)+(15.042), (I.81)+(15.043), (I.81)+(15.044), (I.81)+(15.045), (I.81)+(15.046), (I.81)+(15.047), (I.81)+(15.048), (I.81)+(15.049), (I.81)+(15.050), (I.81)+(15.051), (I.81)+(15.052), (I.81)+(15.053), (I.81)+(15.054), (I.81)+(15.055), (I.81)+(15.056), (I.81)+(15.057), (I.81)+(15.058), (I.81)+(15.059), (I.81)+(15.060), (I.81)+(15.061), and (I.81)+(15.062).

In certain embodiments, the active compound or combination of active compounds are selected from the group (G4) consisting of the following mixtures: (I.91)+(1.001), (I.91)+(1.002), (I.91)+(1.003), (I.91)+(1.004), (I.91)+(1.005), (I.91)+(1.006), (I.91)+(1.007), (I.91)+(1.008), (I.91)+(1.009), (I.91)+(1.010), (I.91)+(1.011), (I.91)+(1.012), (I.91)+(1.013), (I.91)+(1.014), (I.91)+(1.015), (I.91)+(1.016), (I.91)+(1.017), (I.91)+(1.018), (I.91)+(1.019), (I.91)+(1.020), (I.91)+(1.021), (I.91)+(1.022), (I.91)+(1.023), (I.91)+(1.024), (I.91)+(1.025), (I.91)+(1.026), (I.91)+(1.027), (I.91)+(1.028), (I.91)+(1.029), (I.91)+(1.030), (I.91)+(1.031), (I.91)+(1.032), (I.91)+(1.033), (I.91)+(1.034), (I.91)+(1.035), (I.91)+(1.036), (I.91)+(1.037), (I.91)+(1.038), (I.91)+(1.039), (I.91)+(1.040), (I.91)+(1.041), (I.91)+(1.042), (I.91)+(1.043), (I.91)+(1.044), (I.91)+(1.045), (I.91)+(1.046), (I.91)+(1.047), (I.91)+(1.048), (I.91)+(1.049), (I.91)+(1.050), (I.91)+(1.051), (I.91)+(1.052), (I.91)+(1.053), (I.91)+(1.054), (I.91)+(1.055), (I.91)+(1.056), (I.91)+(1.057), (I.91)+(1.058), (I.91)+(1.059), (I.91)+(1.060), (I.91)+(1.061), (I.91)+(1.062), (I.91)+(1.063), (I.91)+(1.064), (I.91)+(1.065), (I.91)+(1.066), (I.91)+(1.067), (I.91)+(1.068), (I.91)+(1.069), (I.91)+(1.070), (I.91)+(1.071), (I.91)+(1.072), (I.91)+(1.073), (I.91)+(1.074), (I.91)+(1.075), (I.91)+(1.076), (I.91)+(1.077), (I.91)+(1.078), (I.91)+(1.079), (I.91)+(1.080), (I.91)+(1.081), (I.91)+(1.082), (I.91)+(2.001), (I.91)+(2.002), (I.91)+(2.003), (I.91)+(2.004), (I.91)+(2.005), (I.91)+(2.006), (I.91)+(2.007), (I.91)+(2.008), (I.91)+(2.009), (I.91)+(2.010), (I.91)+(2.011), (I.91)+(2.012), (I.91)+(2.013), (I.91)+(2.014), (I.91)+(2.015), (I.91)+(2.016), (I.91)+(2.017), (I.91)+(2.018), (I.91)+(2.019), (I.91)+(2.020), (I.91)+(2.021), (I.91)+(2.022), (I.91)+(2.023), (I.91)+(2.024), (I.91)+(2.025), (I.91)+(2.026), (I.91)+(2.027), (I.91)+(2.028), (I.91)+(2.029), (I.91)+(2.030), (I.91)+(2.031), (I.91)+(2.032), (I.91)+(2.033), (I.91)+(2.034), (I.91)+(2.035), (I.91)+(2.036), (I.91)+(2.037), (I.91)+(2.038), (I.91)+(2.039), (I.91)+(2.040), (I.91)+(2.041), (I.91)+(2.042), (I.91)+(2.043), (I.91)+(2.044), (I.91)+(2.045), (I.91)+(2.046), (I.91)+(2.047), (I.91)+(2.048), (I.91)+(2.049), (I.91)+(2.050), (I.91)+(2.051), (I.91)+(2.052), (I.91)+(2.053), (I.91)+(2.054), (I.91)+(2.055), (I.91)+(2.056), (I.91)+(3.001), (I.91)+(3.002), (I.91)+(3.003), (I.91)+(3.004), (I.91)+(3.005), (I.91)+(3.006), (I.91)+(3.007), (I.91)+(3.008), (I.91)+(3.009), (I.91)+(3.010), (I.91)+(3.011), (I.91)+(3.012), (I.91)+(3.013), (I.91)+(3.014), (I.91)+(3.015), (I.91)+(3.016), (I.91)+(3.017), (I.91)+(3.018), (I.91)+(3.019), (I.91)+(3.020), (I.91)+(3.021), (I.91)+(3.022), (I.91)+(3.023), (I.91)+(3.024), (I.91)+(3.025), (I.91)+(3.026), (I.91)+(3.027), (I.91)+(3.028), (I.91)+(3.029), (I.91)+(4.001), (I.91)+(4.002), (I.91)+(4.003), (I.91)+(4.004), (I.91)+(4.005), (I.91)+(4.006), (I.91)+(4.007), (I.91)+(4.008), (I.91)+(4.009), (I.91)+(4.010), (I.91)+(4.011), (I.91)+(4.012), (I.91)+(4.013), (I.91)+(4.014), (I.91)+(4.015), (I.91)+(4.016), (I.91)+(4.017), (I.91)+(4.018), (I.91)+(4.019), (I.91)+(4.020), (I.91)+(4.021), (I.91)+(4.022), (I.91)+(4.023), (I.91)+(4.024), (I.91)+(4.025), (I.91)+(5.001), (I.91)+(5.002), (I.91)+(5.003), (I.91)+(5.004), (I.91)+(5.005), (I.91)+

(5.006), (I.91)+(5.007), (I.91)+(5.008), (I.91)+(5.009), (I.91)+(5.010), (I.91)+(5.011), (I.91)+(5.012), (I.91)+(5.013), (I.91)+(5.014), (I.91)+(5.015), (I.91)+(5.016), (I.91)+(5.017), (I.91)+(5.018), (I.91)+(5.019), (I.91)+(5.020), (I.91)+(5.021), (I.91)+(5.022), (I.91)+(5.023), (I.91)+(6.001), (I.91)+(6.002), (I.91)+(6.003), (I.91)+(6.004), (I.91)+(7.001), (I.91)+(7.002), (I.91)+(7.003), (I.91)+(7.004), (I.91)+(7.005), (I.91)+(7.006), (I.91)+(8.001), (I.91)+(9.001), (I.91)+(9.002), (I.91)+(9.003), (I.91)+(9.004), (I.91)+(9.005), (I.91)+(9.006), (I.91)+(9.007), (I.91)+(9.008), (I.91)+(9.009), (I.91)+(10.001), (I.91)+(10.002), (I.91)+(10.003), (I.91)+(11.001), (I.91)+(11.002), (I.91)+(12.001), (I.91)+(12.002), (I.91)+(12.003), (I.91)+(12.004), (I.91)+(13.001), (I.91)+(13.002), (I.91)+(13.003), (I.91)+(13.004), (I.91)+(13.005), (I.91)+(13.006), (I.91)+(14.001), (I.91)+(14.002), (I.91)+(15.001), (I.91)+(15.002), (I.91)+(15.003), (I.91)+(15.004), (I.91)+(15.005), (I.91)+(15.006), (I.91)+(15.007), (I.91)+(15.008), (I.91)+(15.009), (I.91)+(15.010), (I.91)+(15.011), (I.91)+(15.012), (I.91)+(15.013), (I.91)+(15.014), (I.91)+(15.015), (I.91)+(15.016), (I.91)+(15.017), (I.91)+(15.018), (I.91)+(15.019), (I.91)+(15.020), (I.91)+(15.021), (I.91)+(15.022), (I.91)+(15.023), (I.91)+(15.024), (I.91)+(15.025), (I.91)+(15.026), (I.91)+(15.027), (I.91)+(15.028), (I.91)+(15.029), (I.91)+(15.030), (I.91)+(15.031), (I.91)+(15.032), (I.91)+(15.033), (I.91)+(15.034), (I.91)+(15.035), (I.91)+(15.036), (I.91)+(15.037), (I.91)+(15.038), (I.91)+(15.039), (I.91)+(15.040), (I.91)+(15.041), (I.91)+(15.042), (I.91)+(15.043), (I.91)+(15.044), (I.91)+(15.045), (I.91)+(15.046), (I.91)+(15.047), (I.91)+(15.048), (I.91)+(15.049), (I.91)+(15.050), (I.91)+(15.051), (I.91)+(15.052), (I.91)+(15.053), (I.91)+(15.054), (I.91)+(15.055), (I.91)+(15.056), (I.91)+(15.057), (I.91)+(15.058), (I.91)+(15.059), (I.91)+(15.060), (I.91)+(15.061), and (I.91)+(15.062).

In certain embodiments, the active compound or combination of active compounds are selected from the mixtures belonging to group (G1) or (G2).

In certain embodiments, the active compound or combination of active compounds are selected from the group (G1-A) consisting of the following mixtures: (I.01)+(1.012), (I.01)+(1.018), (I.01)+(1.020), (I.01)+(1.021), (I.01)+(2.002), (I.01)+(2.005), (I.01)+(2.017), (I.01)+(2.027), (I.01)+(2.038), (I.01)+(3.020), (I.01)+(3.025), (I.01)+(4.005), (I.01)+(5.004), (I.01)+(5.013), (I.01)+(5.018), (I.01)+(12.003), (I.01)+(12.004), (I.01)+(13.001), (I.01)+(13.004), (I.01)+(15.008), (I.01)+(15.047).

In certain embodiments, the active compound or combination of active compounds are selected from the group (G2-A) consisting of the following mixtures: (I.59)+(1.012), (I.59)+(1.018), (I.59)+(1.020), (I.59)+(1.021), (I.59)+(2.002), (I.59)+(2.005), (I.59)+(2.017), (I.59)+(2.027), (I.59)+(2.038), (I.59)+(3.020), (I.59)+(3.025), (I.59)+(4.005), (I.59)+(5.004), (I.59)+(5.013), (I.59)+(5.018), (I.59)+(12.003), (I.59)+(12.004), (I.59)+(13.001), (I.59)+(13.004), (I.59)+(15.008), (I.59)+(15.047).

In certain embodiments, the active compound or combination of active compounds are selected from the group (G3-A) consisting of the following mixtures: (I.81)+(1.012), (I.81)+(1.018), (I.81)+(1.020), (I.81)+(1.021), (I.81)+(2.002), (I.81)+(2.005), (I.81)+(2.017), (I.81)+(2.027), (I.81)+(2.038), (I.81)+(3.020), (I.81)+(3.025), (I.81)+(4.005), (I.81)+(5.004), (I.81)+(5.013), (I.81)+(5.018), (I.81)+(12.003), (I.81)+(12.004), (I.81)+(13.001), (I.81)+(13.004), (I.81)+(15.008), (I.81)+(15.047).

In certain embodiments, the active compound or combination of active compounds are selected from the group (G4-A) consisting of the following mixtures: (I.91)+(1.012), (I.91)+(1.018), (I.91)+(1.020), (I.91)+(1.021), (I.91)+(2.002), (I.91)+(2.005), (I.91)+(2.017), (I.91)+(2.027), (I.91)+(2.038), (I.91)+(3.020), (I.91)+(3.025), (I.91)+(4.005), (I.91)+(5.004), (I.91)+(5.013), (I.91)+(5.018), (I.91)+(12.003), (I.91)+(12.004), (I.91)+(13.001), (I.91)+(13.004), (I.91)+(15.008), (I.91)+(15.047).

In certain embodiments, the active compound or combination of active compounds are selected from the mixtures belonging to group (G1-A) or (G2-A).

In certain embodiments, the active compound or combination of active compounds can be present in a broad range of effective weight ratio of A:B, for example in a range of 100:1 to 1:100, preferably in a weight ratio of 50:1 to 1:50, most preferably in a weight ratio of 20:1 to 1:20. Further ratios of A:B which can be used according to the present invention with increasing preference in the order given are: 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Where a compound (A) or a compound (B) can be present in isomeric forms and/or tautomeric forms, such a compound is understood hereinabove and hereinbelow also to include, where applicable, corresponding isomeric and/or tautomeric forms or mixtures thereof, even when these are not specifically mentioned in each case.

V. DEFINITIONS

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which tomato plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of tomato breeding. An "elite population" is an assortment of elite individuals or varieties that can be used to represent the state of the art in terms of agronomically superior genotypes of a given crop species, such as tomato. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "tolerance locus" means a locus associated with tolerance or resistance to disease. For instance, a tolerance locus according to the present invention may, in one embodiment, control tolerance or susceptibility to Fol.

As used herein, "tolerance" or "improved tolerance" in a plant refers to the ability of the plant to perform well, for example by maintaining yield, under disease conditions. Tolerance may also refer to the ability of a plant to maintain a plant vigor phenotype under disease conditions. Tolerance is a relative term, indicating that a "tolerant" plant is more able to maintain performance compared to a different (less tolerant) plant (e.g. a different plant variety) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance of different plants, plant varieties, or plant families under disease conditions, and furthermore, will also recognize the phenotypic gradations of "tolerance."

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

As used herein, "resistance allele" means the nucleic acid sequence associated with tolerance or resistance to disease.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. DEPOSIT INFORMATION

A deposit was made of at least 2500 seeds of tomato line FDS-ZJ11002, which comprises the reduced 1-3 introgression described herein. The deposit was made with the American Type Culture Collection (ATCC), 10801 University Boulevard, Manassas, Va. 20110-2209 USA. The deposit is assigned ATCC Accession No. PTA-124465, and the date of deposit was Sep. 11, 2017. Access to the deposit will be available during the pendency of the application to persons entitled thereto upon request. The deposit has been accepted under the Budapest Treaty and will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

EXAMPLES

Example 1. Determining Fruit Firmness

The fruit firmness trait is heavily influenced by environmental factors. Tomato fruit softens as part of the ripening process, and the speed of the ripening process is influenced by genetics and environmental factors. It is therefore important that each experiment includes positive and negative control lines to ensure that differences in firmness, or the lack thereof, are the result of a correctly performed experiment, rather than measuring at the wrong ripening stage. Furthermore, it is important to calibrate the speed of ripening for each genotype used in an experiment. Fruit maturity is quantified as the number of days past the breaker stage, which is defined as a definite break in color from green to tannish-yellow, pink or red on not more than 10% of the fruit surface often at the blossom end of the fruit. The fruit softness is measured when the fruit are fully ripened at the red stage, which is defined as the moment that more than 90% of the surface has reached the mature fruit color. The mature color is often red, but can also be pink, yellow, or orange. To calibrate the time to fruit maturity, one should frequently check the fruits at the blossom end for changes in fruit color indicating the breaker stage. Fruit that reaches this stage should be marked, preferably marked in such a way that it is clear when the fruit entered the breaker stage. The marked fruit should be tracked daily to follow it through the different ripening stages until has reached a point where it stops changing color and darkening, which is the ideal moment to measure fruit firmness. This point is typically reached 7 to 14 days post breaker stage. In the same experiment fruit that reached the breaker stage later than the calibration set can be used to determine fruit firmness for the actual experiment. Fruit that are affected by disease, cracking, blossom end rot, sun scald, and any other factor that affects the fruit quality should be excluded from the experiment. In addition, care should be taking during harvest, handling and transport not to avoid bruising. The fruit should not be stacked and should be moved gently.

Fruit firmness was measured with a squishometer, which is essentially an apparatus that compresses the fruit with a fixed force between a plexiglass disc and a metal platform and measures the deformation of the whole fruit. Deformation in a squishometer was measured in two directions: 1) between crown and bottom; and 2) between the sides. Two forces were used to measure the distance of deformation of the fruit: 1300 g/in$^2$ and 2600 g/in$^2$. The more the deformation of the fruit the softer the fruit. Alternatively, a durometer can be used to measure firmness. A durometer measures the firmness with a small pin and thus determines local firmness instead of measuring the firmness of a whole fruit.

Example 2. Mapping of Soft Fruit Alleles

The I-3 resistance gene is located on chromosome 7 and it has been determined that RFLP marker TG217 is closely linked with the I-3 locus (within 2 cM). However, the present inventors have discovered that I-3 introgressions comprise deleterious soft fruit alleles, leading to unacceptable fruit quality when I-3 alleles are introgressed into elite tomato lines. To map the location of the soft fruit alleles in order to uncouple them from the I-3 gene, a mapping population was created using a breeding line containing the I-3 resistance from FL7547 (FIR-15-2116) and a susceptible line (FIS-18-2086). The F2 population from this cross was screened for recombinants using two newly developed SNP markers M5 and M6. These markers were chosen from candidate markers in a 6-10 cM region surrounding the TG217 locus. In the region between M5 and M6, seven additional SNP markers were developed to identify recombination breakpoints in the I-3 region (Table 1). It was found that of the 234 recombinants found in the F2, 98% had a recombination event located between the northern flanking marker M5 and the original trait associated marker TG217 located between 61,390,747 bp and 61,392,044 bp of chromosome 7 of the public tomato genome sequence SL2.40. The other 2% had a recombination event between TG217 and the southern flanking marker M6. Twelve new SNP markers were developed in the region south of TG217. Some of these markers were between TG217 and M6, but most were south of M6 increasing the physical and genetic region of what is perceived to be the region containing the I-3 gene. Public marker SLG-1 (Lim, et al., 2008) was identified as the new I-3 resistance associated marker replacing TG217. However, SLG-1 is unsuitable in a high-throughput commercial setting because it is a marker that requires a restriction enzyme analysis to determine the allele. This type of marker is time consuming to run and has been surpassed by TAQman-based markers. Thus the SLG-1 marker was used as a basis to develop a trait-linked TAQMan marker.

TABLE 1

| | | | | | | | | | | | |
|---|---|---|---|---|---|---|---|---|---|---|---|
| Markers used in the fine mapping of FoL Race 3 resistance QTLs. | | | | | | | | | | | |
| Marker Name | Genetic Map Position (cM) | Public Chr. | Public Position of SNP SL2.40 (bp) | Marker Size (bp) | SNP Position in Marker (bp) | SNP Change | Marker Sequence (SEQ ID NO.) | Fwd Primer (SEQ ID NO.) | Rev Primer (SEQ ID NO.) | Probe 1 (SEQ ID NO.) | Probe 2 (SEQ ID NO.) |
| M1 | 72.75 | 7 | 60,912,462 | 643 | 124 | [A/G] | 1 | 2 | 3 | 4 | 5 |
| M2 | 72.75 | 7 | 60,956,224 | 547 | 123 | [A/G] | 6 | 7 | 8 | 9 | 10 |

A BC2F5 population was developed from the above-described F2 population and plants were trialed for fruit firmness. For each family 2 genotypic classes were used. The original population parents, FIR-15-2116 (I-3 donor with undesirable soft fruit alleles) and FIS-18-2086 (susceptible parent without soft fruit linkage drag), and further soft and firm fruit controls were included in the trial. The trial was set up using a split plot design with each plot being one of the paired lines from the same F2 family. Each plot thus consisted of fixed recombinants and their homozygous controls. The soft and firm controls were paired in a plot, as were the parental controls. The plots were placed randomly, with 10 replications. Each plot contained 4 plants. Each plot was harvested 4 times for fruit firmness determination, whereby 4 fruit per plant were harvested. The firmness data points were averaged to produce one LSMean per plot. Subsequent genetic analysis showed that recombinants with a breaking point between M1 (SEQ ID NO:1) and M2 (SEQ ID NO:6) lost the soft fruit phenotype when a S. lycopersicum allele was detected at M1 (Table 2).

TABLE 2

Genetic and fruit firmness analysis of recombinant populations. A recombination event between M1 and M2 leads to resistant plants with an absence of soft fruit alleles. P stands for a *S. pennellii* allele, while E stands for a *S. lycopersicum* allele. Squisho values are mm of compression under a certain pressure. A higher Squisho value means softer fruit.

| Entry | M7 | M8 | M9 | M6 | M1 | M2 | M10 | M11 | M12 | Family | Generation | LSM 1300 g Squisho | LSM 2600 g Squisho |
|---|---|---|---|---|---|---|---|---|---|---|---|---|---|
| 1 | P | P | P | P | P | E | E | E | E | 5816 | BC2F5 | 2.691 | 5.107 |
| 2 | E | E | E | E | E | E | E | E | E | 5816 | BC2F5 | 2.462 | 4.634 |
| 3 | E | E | E | E | E | P | P | P | P | 5806 | BC2F5 | 1.934 | 3.701 |
| 4 | E | E | E | E | E | P | P | P | P | 5806 | BC2F5 | 1.948 | 3.746 |
| 5 | P | P | P | P | P | E | E | E | E | 5810 | BC2F4 | 2.099 | 3.967 |
| 6 | P | P | P | P | P | P | P | P | P | 5810 | BC2F4 | 2.05 | 3.886 |
| 7 | E | E | E | E | E | E | E | E | E | RP | IB | 1.963 | 3.734 |
| 8 | P | P | P | P | P | P | P | P | P | RP | BC2F3 | 2.123 | 4.048 |

Example 3. Developing the I-3 Breeding Event

Due to the low recombination rate between markers M1 and M2 (overlapping genetic positions on chromosome 7) a breeding event donor was developed that could be used as an I-3 donor for all breeding programs. Entry 3 (Table 2) was chosen and finished as FDS-ZJ11002, and a sample of seed of this line has been deposited under ATCC Accession No. PTA-124465. This line was subsequently tested for *Fusarium oxysporum* f. sp. *Lycopersici* Race 3 resistance and found to be highly resistant. To better understand the I-3 introgression present in FDS-ZJ11002, a sequence capture analysis was done and it was found that the southern breaking point of the *S. pennellii* introgression was between SNPs M3 and M4 (FIG. 1). M3 is located at 61,095,125 bp of the public tomato genome SL2.40, while M4 is located at 61,106,828 bp of the public tomato genome SL2.40. Therefore, the total size of the I-3 introgression in the FDS-ZJ11002 germplasm is at least 138,901 bp and at most 194,366 bp per the public genome sequence SL2.40. In contrast, public versions of the I-3 introgression extend to TG572 or beyond. TG572 is located between 61,390,747 bp and 61,392,044 bp of chromosome 7 of the public tomato genome sequence SL2.40.

What is claimed is:

1. A tomato plant of a cultivated variety or plant part thereof comprising a recombinant chromosomal segment on chromosome 7, wherein said chromosomal segment comprises a *Fusarium oxysporum* f. sp. *lycopersici* (Fol) resistance allele conferring to said plant increased resistance to Fol compared to a plant not comprising said allele, and wherein said chromosomal segment lacks a deleterious allele genetically linked to said Fol resistance allele that confers a soft fruit trait to said plant when present, and wherein said tomato plant further comprises a non-introgressed allele at marker locus M4 (SEQ ID NO:12), and wherein said recombinant chromosomal segment is flanked by M1 (SEQ ID NO: 1) and M4 (SEQ ID NO: 12).

2. The tomato plant of claim 1, wherein said recombinant chromosomal segment is flanked in the genome of said plant by marker locus M1 (SEQ ID NO:1) and marker locus M3 (SEQ ID NO:11) on chromosome 7,
   wherein said Fol resistance allele is within a recombinant chromosomal segment on chromosome 7 comprising marker locus M2 (SEQ ID NO:6);
   wherein said chromosomal segment is derived from a plant of line FDS-ZJ11002, a sample of seed of said line having been deposited under ATCC Accession No. PTA-124465; or
   wherein said tomato plant comprises a non-introgressed allele at marker locus M1 (SEQ ID NO:1) and an introgressed allele at marker locus M2 (SEO ID NO:6).

3. The tomato plant of claim 1, wherein a representative sample of seed comprising said chromosomal segment has been deposited under ATCC Accession No. PTA-124465.

4. A tomato plant, cell, or seed of tomato line FDS-ZJ11002, wherein a sample of seed of said line has been deposited under ATCC Accession No. PTA-124465, and wherein said tomato plant, cell, or seed shares the genotype of tomato line FDS-ZJ11002.

5. A method of producing a tomato plant exhibiting resistance to Fol, comprising:
   a) crossing the tomato plant of claim 1 with itself or with a second tomato plant of a different genotype to produce one or more progeny plants; and
   b) selecting a progeny plant comprising said Fol resistance allele.

6. The method of claim 5, wherein said progeny plant is an $F_2$-$F_6$ progeny plant.

7. The method of claim 5, wherein producing said progeny plant comprises backcrossing.

8. A method of selecting a tomato plant exhibiting resistance to Fol, comprising:
   a) crossing the tomato plant of claim 1 with itself or with a second tomato plant of a different genotype to produce one or more progeny plants; and
   b) selecting a progeny plant comprising said Fol resistance allele.

9. The method of claim 8, wherein said progeny plant is an $F_2$-$F_6$ progeny plant.

10. The method of claim 8, wherein producing said progeny plant comprises backcrossing.

* * * * *

UNITED STATES PATENT AND TRADEMARK OFFICE
CERTIFICATE OF CORRECTION

| | |
|---|---|
| PATENT NO. | : 11,479,788 B2 |
| APPLICATION NO. | : 16/218261 |
| DATED | : October 25, 2022 |
| INVENTOR(S) | : Graham et al. |

It is certified that error appears in the above-identified patent and that said Letters Patent is hereby corrected as shown below:

On the Title Page

Item (71) Applicant, please delete "Seminis Vegetable Seeds, inc." and insert --Seminis Vegetable Seeds, Inc.--

Signed and Sealed this
Eighteenth Day of June, 2024

Katherine Kelly Vidal
*Director of the United States Patent and Trademark Office*